United States Patent [19]
Ho et al.

[11] Patent Number: 5,714,141
[45] Date of Patent: Feb. 3, 1998

[54] USE OF INTERLEUKIN 7 TO ENHANCE HUMORAL IMMUNITY

[75] Inventors: Rodney Jin Yong Ho, Seattle, Wash.; Connie Rene Faltynek, Wayne, Pa.

[73] Assignee: University of Washington, Seattle, Wash.

[21] Appl. No.: 458,032

[22] Filed: Jun. 1, 1995

Related U.S. Application Data

[63] Continuation of Ser. No. 41,672, Apr. 1, 1993, abandoned.

[51] Int. Cl.$^6$ .......................... A61K 45/05; A61K 9/127; A61K 39/38; C07K 1/00
[52] U.S. Cl. .................. 424/85.2; 424/231.1; 424/234.1; 424/184.1; 424/450; 530/350
[58] Field of Search .......................... 424/184.1, 188.1, 424/204.1, 186.1, 234.1, 265.1, 274.1, 85.2, 85.1, 417, 450; 530/351, 350

[56] References Cited

U.S. PATENT DOCUMENTS 4,965,195 10/1990 Namen et al. .................. 435/69.52

OTHER PUBLICATIONS

Hock et al., Interleukin 7 Induces CD4$^+$ Cell-dependent Tumor Rejection, *J. Exp. Med.*, vol. 174, Dec. 1991, pp. 1291–1298.

Aoki et al., Expression of Murine interleukin 7 in a murine glioma cell line results in reduced tumorigenicty *in vivo*, *Proc. Natl. Acad. Sci. USA*, vol. 89, May 1992, pp. 3850–3854.

McBride et al., Genetic Modification of a Murine Fibrosarcoma to Produce Interleukin 7 Stimulates Host Cell Infiltration and Tumor Immunity, *Cancer Res.*, vol. 52, Jul. 1992, pp. 3931–3937.

Chazen, et al., "Interleukin 7 is a T–Cell Growth Factor", *Proc. Natl. Acad. Sci.*, 86:5923–5927, Aug., 1989.

Grabstein, et al., "Regulation of T Cell Proliferation by IL–7", *J. of Immuno.*, 144:3015–3020, Apr. 15, 1990.

Alderson, "Interleukin 7 Enhances Cytolytic T Lymphocyte Generation adn Induces Lymphokine–activated Killer Cells from Human Peripheral Blood", *J. Exp. Med.*, 172:577–587, Aug. 1990.

Naylor, et al. 1982, "In vivo induction of . . . " Infection and Immunity 36(3):1209–1216.

Hickman, et al, 1990, "Regulation of human cytotoxic T . . . " J. Immunol, 145(8):2415–2420.

Ho, et al, 1992, "Liposome–formulated interleukin–2 . . . " Vaccine 10(4):209–213.

Daniel, et al, 1992, "Protective effects of a live alternated SIV Vaccine . . ." Science 258:1938–41.

*Primary Examiner*—Lynette F. Smith
*Attorney, Agent, or Firm*—Townsend and Townsend and Crew

[57] ABSTRACT

The present invention is directed to a method of improving the potency of a vaccine in a mammalian host comprising administering a therapeutically effective amount of a vaccine and a potency improving amount of IL-7. In a preferred embodiment, the IL-7 is dissolved or dispersed in a pharmaceutically acceptable carrier. The pharmaceutically acceptable carrier is preferably in the form of a lipid dispersion.

20 Claims, 9 Drawing Sheets

FIG. 1A
FIG. 1B
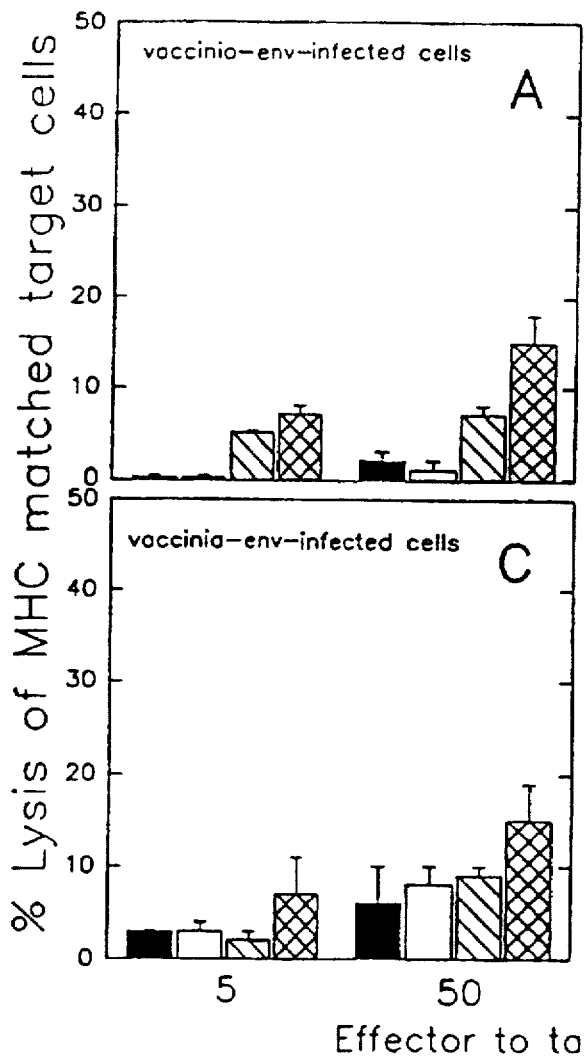
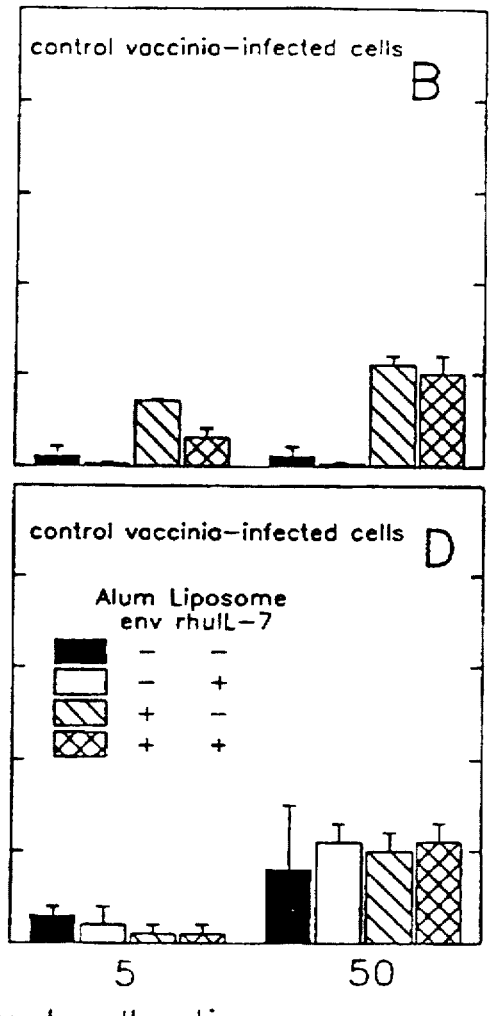
FIG. 1C
FIG. 1D

FIG. 4A
FIG. 4B
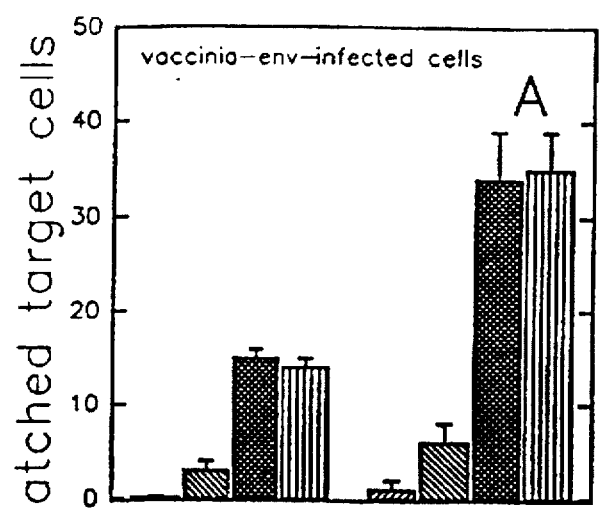
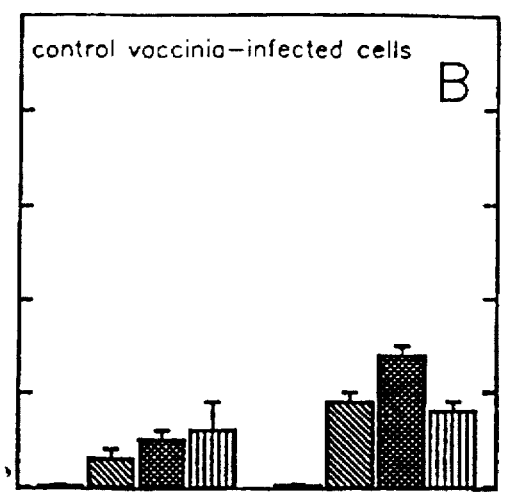
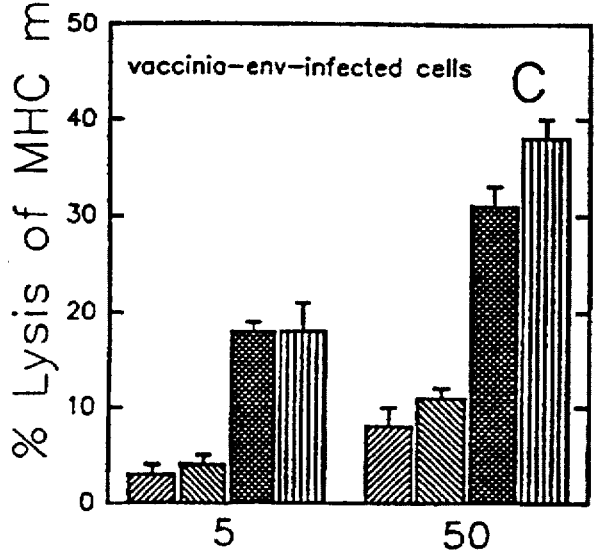
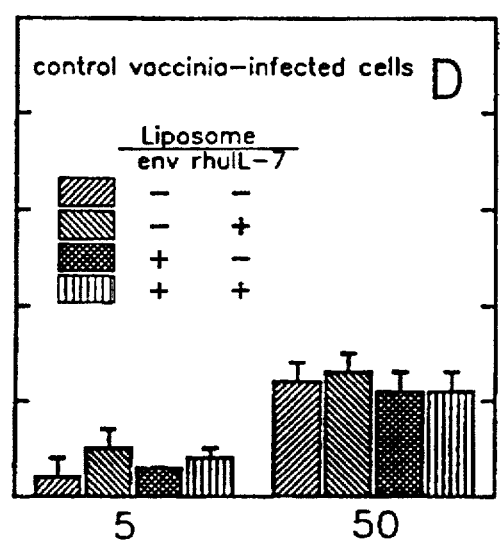
FIG. 4C
FIG. 4D

USE OF INTERLEUKIN 7 TO ENHANCE HUMORAL IMMUNITY

This is a continuation of application Ser. No. 08/041,672, filed Apr. 1, 1993, now abandoned.

This invention was made with government support under grant number AI31854 awarded by the National Institutes of Health. The government has certain rights in this invention.

FIELD OF THE INVENTION

The present invention is directed to the improvement of vaccine potency. More specifically, the present invention is directed to the improvement of prophylactic vaccination by the use of interleukin-7 in a pharmaceutical preparation.

BACKGROUND OF THE INVENTION

Interleukin-7 (IL-7), which is a 25 kilodalton cytokine originally derived from a bone marrow stromal cell line, stimulates the proliferation of B-cell progenitors. However, IL-7, like other interleukin proteins, has pleiotropic effects on a wide variety of lymphoid cells. Results from in vitro experiments indicate that IL-7 can also stimulate both immature and mature T cells. Murine IL-7 and human IL-7 have been cloned, and exhibit about 60% homology. The human form of IL-7 can stimulate both human and murine lymphocytes.

Administration of recombinant human or murine IL-7 to normal mice primarily increases the precursor and mature B lymphocytes while having some effect on T lymphocytes. Recombinant IL-7 has also been shown to accelerate the recovery of lymphocytes in either cyclophosphamide-treated or sublethally irradiated, immune-suppressed mice.

BRIEF DESCRIPTION OF THE INVENTION

The present invention is directed to a method of improving vaccine potency in a mammalian host comprising administering a therapeutically effective amount of IL-7. In a preferred embodiment, the IL-7 is dissolved or dispersed in a pharmaceutically acceptable carrier. The pharmaceutically acceptable carrier is preferably in the form of a lipid dispersion. In a preferred embodiment, the lipid dispersion consists of liposomes.

In a preferred embodiment, the vaccine is one which is used to prevent a microbial infection. The microbial infection is preferably caused by a virus, fungus, yeast, bacterium or protozoan agent. In a more preferred embodiment, the causative agent is the herpes simplex virus (HSV) or the human immunodeficiency virus (HIV).

The IL-7 used in the method of the present invention is preferably recombinant human or recombinant murine IL-7.

Preferably, the vaccine and the IL-7 are administered simultaneously. In another preferred embodiment, the vaccine and the IL-7 are administered sequentially.

The present invention is further directed to a method of improving the potency of a vaccine comprising adding a potency improving amount of IL-7 to a vaccine.

The present invention is still further directed to a vaccine composition for improving vaccine potency in a mammalian host comprising a therapeutically effective amount of IL-7 and a therapeutically effective amount of a vaccine. The vaccine composition is preferably dissolved or dispersed in a pharmaceutically acceptable carrier.

In a preferred embodiment, the vaccine comprises a microbial antigen. The microbial antigen is preferably a viral antigen. In a preferred embodiment, the viral antigen is recombinant HIV envelope protein env 2-3 or HSV glycoprotein D.

BRIEF DESCRIPTION OF THE FIGURES

FIGS. 1A–1D. The effects of liposome encapsulated recombinant human IL-7 (rhuIL-7) administration on cytolytic activity against vaccinia-env virus infected MHC matched cells are shown. Spleen cells from mice that had been immunized with alum associated env-2-3 (striped or hatched bars) or control (OVA) (filled or open bars), as well as given either rhuIL-7 liposomes (open or hatched bars) or empty liposomes (filled or striped bars), were used as effector cells. MHC matched EMT6 cells were infected with vaccinia virus expressing env proteins (A and C) or control vaccinia virus (B and D) and were used as target cells. Cytolytic activity is expressed as percent of total lysis for spleen cells harvested on day 21 (A and B) and on day 35/42 (C and D). Data expressed were mean ±standard deviation (S.D.) percent lysis activity of each treatment group determined at effector to target ratios of 5:1 and 50:1.

FIGS. 4A–4D. The effects of liposome encapsulated rhuIL-7 administration on cytolytic activity against vaccinia-env virus infected MHC matched cells are shown. Mice were immunized with env-2-3 (hatched or lined bars) or ovalbumin (left or right striped bars) formulated in muramyltripeptide-phosphatidylethanolamine (MTP-PE) liposomes and were also given either rhuIL-7 liposomes (right striped or lined bars) or empty liposomes (left striped or hatched bars) as described in the treatment protocol; their spleen mononuclear cells were used as effector cells. MHC matched EMT6 cells were infected with vaccinia virus expressing env proteins (A and C) or control vaccinia virus (B and D) and were used as target cells. Cytolytic activity is expressed as percent of total lysis for spleen cells harvested on day 21 (A and B) and on day 35/42 (C and D). Data expressed were mean ±S.D. percent lysis activity of each treatment group determined at effector to target ratios of 5:1 and 50:1.

DETAILED DESCRIPTION OF THE INVENTION

Figure 2A:
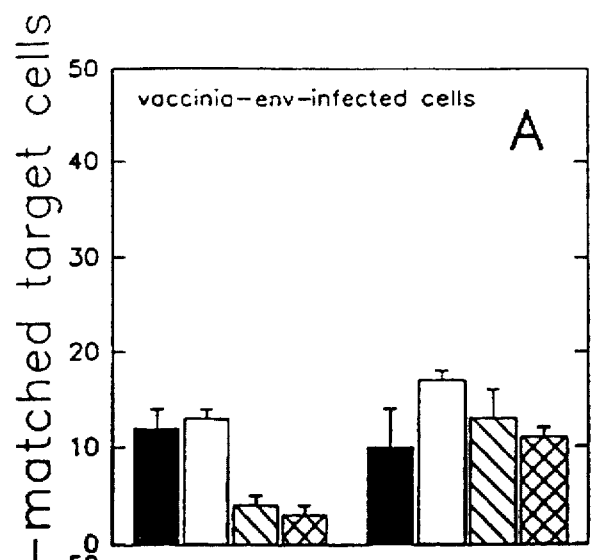
FIGS. 2A–2D. The effects of liposome encapsulated rhuIL-7 administration on cytolytic activity against vaccinia-env virus infected MHC mismatched target cells are shown. Spleen cells from mice that had been immunized with alum associated env-2-3 (striped or hatched bars) or control (OVA) (filled or open bars), as well as given either rhuIL-7 liposomes (open or hatched bars) or empty liposomes (filled or striped bars), were used as effector cells. MHC mismatched L929 cells were infected with vaccinia virus expressing env proteins (A and C) or control vaccinia virus (B and D) and were used as target cells. Cytolytic activity is expressed as percent of total lysis for spleen cells harvested on day 21 (A and B) and on day 35/42 (C and D). Data expressed were mean ±S.D. percent lysis activity of each treatment group determined at effector to target ratios of 5:1 and 50:1.
Figure 2B:
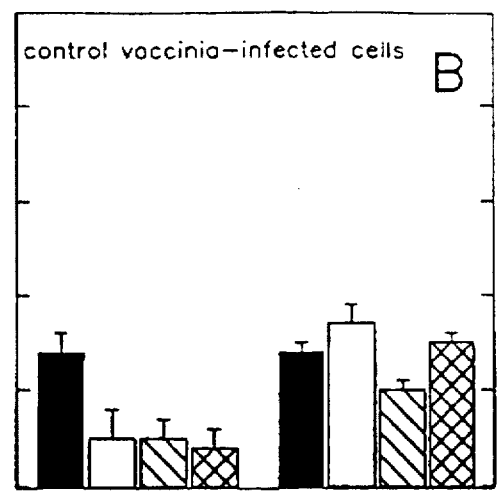
Figure 2C:
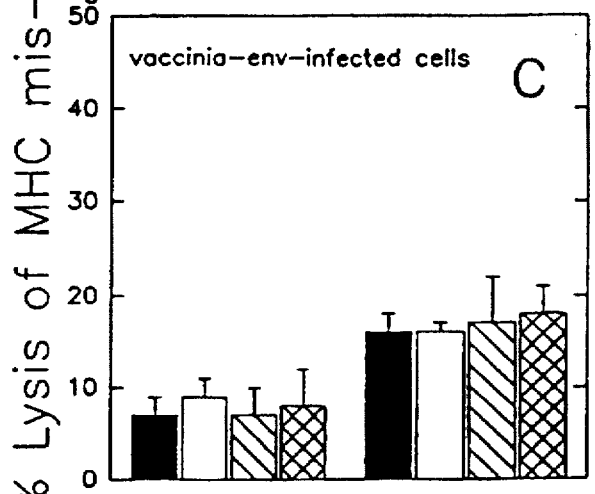
Figure 2D:
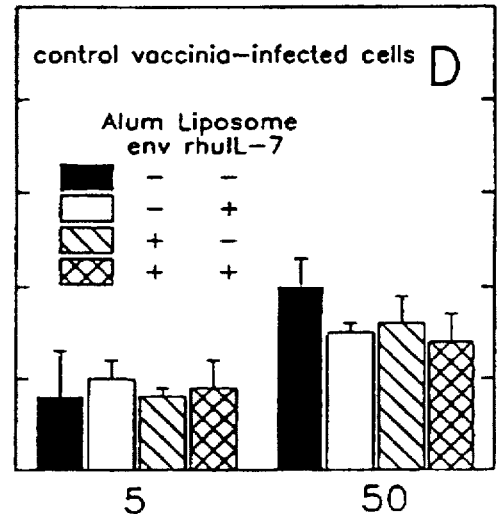

The present invention is directed to a method of improving the potency of a vaccine in a mammalian host comprising the steps of administering a therapeutically effective amount of a vaccine to the host mammal and administering a potency improving amount of IL-7.

A vaccine can be defined as an antigenic preparation administered to a mammalian host in order to stimulate the mammalian host's protective immunity to one or more particular pathogens and/or toxins. Singleton et al. (eds.), Dictionary of Microbiology and Molecular Biology, John Wiley and Sons, Chichester, England (1987). There are at least six major types of vaccines: inactivated vaccines, attenuated vaccines, toxoids, antigenic extracts (purified or partially purified antigen), synthetic vaccines, and genetically engineered vaccines. Thus, a mammalian host may be vaccinated (immunized) against polio by the use of either an inactivated or attenuated vaccine, whereas vaccination (immunization) against tetanus is via the use of tetanus toxoid. Vaccination against a microbial infection may be by the use of an inactivated agent (e.g., killed Bordetella pertussis in the case of pertussis vaccine), attenuated agent (e.g., BCG in the case of tuberculosis vaccine), or purified antigen (e.g., purified polysaccharide from Neisseria meningitidis in the case of meningitis vaccine). The prevention of the growth or establishment of a tumor may be accomplished through the use of a purified or partially purified antigen vaccine, or by the use of the tumor cells themselves (in a protocol analogous to the use of attenuated or killed microbial vaccines).

A microbial infection can be caused by a wide variety of microorganisms, and is classically denoted by the presence of inflammation at the site of infection. Modern medicine recognizes that microbial infections can be accompanied by a variety of symptoms with or without inflammation. However, the particular symptomology must be correlated with the presence of a microbial agent responsible for the disease state.

The variety of microbial agents capable of causing infection ranges from virulent microorganisms such as Yersinia pestis, the causative agent of plaque, to opportunistic microorganisms, such as Pneumocystis carinii, the causative agent of AIDS-related pneumonia.

The microbial agents can be prokaryotic, such as bacteria (e.g., Yersinia pestis, Pneumocystis carinii), eukaryotic, such as yeast (e.g., Saccharomyces cerevisiae), fungi (e.g., Candida albicans, Cryptococcus neoformans) and protozoa (e.g., Trypanosoma cruzi, Toxoplasma gondii, Leishmania donovani) or viral (e.g., Herpes simplex virus, Human immunodeficiency virus) in origin. A microbial infection can be caused by one or more microbial agents acting either in localized areas or systemically.

Prevention of microbial infections contrasts with the treatment of microbial infections. In the treatment of a microbial infection, the mammalian host exhibits the symptomology of microbial infection, and the causative agent has usually been identified. Treatment typically involves the use of antimicrobial agents, particularly antibiotics.

In prevention of microbial infections, the emphasis is on prophylaxis. The mammalian host is not yet exhibiting the symptomology of infection by a microbial agent, but is at risk for such an infection. For example, the mammalian host can be very young or very old, of which either condition predisposes the mammalian host to infection. The mammalian host can also be immunocompromised by, for example, chemotherapy or an acquired or congenital immunodeficiency. Prophylactic therapy of such individuals is contemplated by the processes and compositions of the present invention.

The above discussion is not to suggest that treatment of a disease state cannot be accomplished through the use of a vaccine. For example, recombinant hepatitis B vaccine is recommended for use in mammalian hosts that have been exposed to hepatitis B. For example, one approved therapeutic use of recombinant hepatitis B vaccine is for individuals known or presumed to have been exposed to hepatitis B virus (e.g., health care workers in contact with suspected carriers). In this therapeutic protocol, the host is treated with human hepatitis B immune globulin followed, within seven days, with an intramuscular dose of hepatitis B vaccine. The host is then vaccinated at one month and six months after the first dose of hepatitis B vaccine. See, e.g., Drug Information for the Health Care Professional, United States Pharmacopeial Convention, 13th ed. (1993); Physicians' Desk Reference, Medical Economics Data, Montvale, N.J. (1993).

A similar therapeutic course is recommended for infants born of hepatitis B surface antigen (HBsAg) positive mothers. Such infants are at high risk of becoming chronic hepatitis B virus carriers. A therapeutic protocol in which the infants were treated at birth with hepatitis B immune globulin, followed by three doses of recombinant hepatitis B vaccine effectively prevented the establishment of the carrier state in treated infants. Physicians' Desk Reference, supra.

In halting or preventing the onset or spread of a cancer or neoplasm, the vaccine protocol focusses on tumor-associated antigens. By immunizing the host with a vaccine comprising the tumor-associated antigen (for example, in the form of the cancer cells themselves (analogous to an attenuated or killed vaccine, discussed elsewhere herein) or in the form of a synthetic or semi-synthetic vaccine) the body can mount a humoral and/or cellular immune response to the tumor. This immune response primes the host to seek out and halt the growth or prevent the establishment of a tumor harboring the same or a related tumor-associated antigen. In this way, the vaccination protocol not only acts prophylactically, but therapeutically as well, for a host harboring a tumor or neoplasm.

Improvements on the potency of a vaccine focus on the degree of enhancement of the vaccination protocol in the presence of the adjuvant as opposed to the vaccination protocol in the absence of the adjuvant. Thus, the ability of a particular vaccination protocol to prevent a microbial infection may be measured against the ability to prevent that microbial infection when the vaccination protocol is supplemented with an adjuvant.

Animal models are one useful way of measuring the increase in the potency of a vaccine through the use of an adjuvant. By first subjecting the animal to a vaccination protocol with or without the adjuvant, and subsequently challenging the animal with a virulent strain of the microbial agent, one can measure parameters such as the onset of disease, the course of the disease, and the resolution of the disease as indicative of the increase in the potency of the vaccine with or without the adjuvant.

Where the vaccination protocol is designed to prevent the growth or establishment of a tumor, a similar animal model system can be used to determine the establishment of the tumor, growth of the tumor, and regression of the tumor as measures of the increased potency of the vaccine protocol in the presence of the adjuvant.

As used herein, a "therapeutically effective amount of a vaccine" is that amount of a vaccine which is sufficient to immunize a host mammal against infection, intoxication or tumor establishment or growth. Means for determining a therapeutically effective amount in a particular subject will depend, as is well known in the art, on the nature of the vaccine used, the mass of the subject being treated, the degree to which the subject is immunocompromised, and the like.

As used herein, a "potency increasing amount of IL-7" is that amount of IL-7 which is sufficient for increasing the potency of a vaccine. Methods for determining a potency increasing amount are discussed elsewhere herein, and means for determining a potency increasing amount in a particular subject will depend, as is well known in the art, on the source of the IL-7 used, the mass of the subject being treated, the degree to which the subject is immunocompromised, and the like.

In a preferred embodiment, the IL-7 is dissolved or dispersed in a pharmaceutically acceptable carrier. Similarly, the vaccine is dissolved or dispersed in a pharmaceutically acceptable carrier. The pharmaceutically acceptable carrier is preferably in the form of a lipid dispersion. In a preferred embodiment, the lipid dispersion consists of liposomes.

As used herein, the phrase "lipid dispersion" refers to a dispersion in which lipids, or more preferably phospholipids, are dispersed in an aqueous medium. Such a dispersion may be in the form of an oil-in-water emulsion, or a water-in-oil emulsion. Such a dispersion may preferably consist of liposomes. It is to be understood that the lipid dispersion may comprise a dispersion, an emulsion, or liposomes, alone or in any combination. Thus, for example, in the preparation of liposomes, some fraction of the preparation may be in the form of a dispersion, an emulsion, or both. The presence of liposomes in a given dispersion can readily be detected, as is well known in the art.

While not wishing to be bound by theory, it is thought that the dispersion serves to increase the half-life of the agent or agents (be they IL-7 or the vaccine) injected into the body. The dispersion keeps the agent (or agents) localized at the site of injection, thus enhancing the immune response to the agent prior to clearing of the agent by other bodily processes.

The compositions can be administered to humans and animals either orally, rectally, parenterally (intravenous, by intramuscularly or subcutaneously), intracisternally, intravaginally, intraperitoneally, locally (powders, ointments or drops), or as a buccal or nasal spray. The compositions are preferably administered via liposomes.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions can also contain additional agents such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Dosage forms for topical administration of a compound of this invention include ointments, powders, sprays and inhalants. The active component is admixed under sterile conditions with a physiologically acceptable carrier and any preservatives, buffers or propellants as may be required. Ophthalmic formulations, eye ointments, powders and solutions are also contemplated as being within the scope of this invention.

The agents can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used in such a dispersion. The present compositions in liposome form can contain stabilizers, preservatives, excipients, and the like in addition to the agent. The preferred lipids are phospholipids and phosphatidyl cholines (lecithins), both natural and synthetic, as well as phosphatidylethanolamine.

Methods of forming liposomes are known in the art. See, for example, Prescott, Ed., *Methods in Cell Biology*, Volume XIV, Academic Press, New York, N.Y. (1976), p. 33 et seq.

Actual dosage levels of active ingredients in the compositions of the present invention may be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors.

The total daily dose of the compounds of this invention administered to a host in single or divided dose may be in amounts, for example, of from about 1 nanomol to about 5 micromols per kilogram of body weight. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

In one embodiment, the vaccine prevents a microbial infection. The microbial infection thus prevented is preferably caused by a virus, fungus, yeast, bacterial or protozoan agent. Exemplary microbial agents are discussed elsewhere herein. In a more preferred embodiment, the causative agent is the herpes simplex virus or the human immunodeficiency virus.

In another embodiment, the vaccine prevents (halts) the growth or establishment of a tumor. For example, the vaccine can be directed to a tumor-associated antigen which, when administered to a mammalian host, prevents the establishment or growth of a tumor. Exemplary tumor-associated antigens include the prostate-specific antigen, the carcinoembryonic antigen, alpha fetoprotein, as well as bladder, breast, colon, liver, lung, ovary, rectum, and testis carcinoma-associated antigens. Many of these tumor-associated antigens are defined (recognized) by monoclonal antibodies that can be obtained from, for example, the American Type Culture Collection (ATCC), Rockville, MD.

The IL-7 used in the methods of the present invention is preferably recombinant IL-7. Recombinant IL-7 is preferably recombinant human or recombinant murine IL-7. Methods of preparing the recombinant form of IL-7 from any source are well known in the art of molecular biology.

The present invention is further directed to a method of improving the potency of a vaccine comprising adding a potency improving amount of IL-7 to a vaccine. The IL-7 is preferably in a pharmaceutically acceptable carrier, as is the vaccine. In a preferred embodiment, the pharmaceutically acceptable carrier is a liposome.

In a preferred embodiment, the IL-7 is administered simultaneously with the vaccine. This preferred administration can be practiced with a composition of the present invention, discussed elsewhere herein. Thus, simultaneous administration involves the administration of a composition of the present invention comprising a potency improving amount of IL-7 and a therapeutically effective amount of a vaccine.

In another preferred embodiment, the IL-7 is administered sequentially with the vaccine. It is to be understood that the order of administration is not essential; IL-7 can be administered first, with the vaccine administered subsequently, or the vaccine can be administered first, with IL-7 administered subsequently. Likewise, the temporal sequence of the sequential administration is not essential; the only relevant time sequence is that the administration of the IL-7 be given, before or after the vaccine, such that the IL-7 has the effect of increasing the potency of the vaccine. Thus, the time between administration of the IL-7 and the vaccine can be measured in terms of several minutes, to several hours, to several days. Thus, the IL-7 can be administered followed virtually immediately with administration of the vaccine, at or near the same site as the IL-7 administration. Similarly, the vaccine can be administered followed virtually immediately with administration of the IL-7, at or near the same site as the vaccine administration. Preferably, the IL-7 is administered within four weeks of the administration of the vaccine, and more preferably within one week, and most preferably within one day.

The IL-7 and vaccine used in this method is as described elsewhere herein.

The present invention is further directed to a vaccine composition for improving the potency of a vaccine in a mammalian host comprising a therapeutically effective amount of IL-7 and a therapeutically effective amount of a vaccine.

The vaccine can be any one of the six major types of vaccines discussed elsewhere herein. Indeed, it is to be understood that any vaccine capable of eliciting an appropriate immune response can be used in the present invention. Preferably, the vaccine is an antigenic extract. A preferred antigenic extract is comprised of a microbial antigen.

A microbial antigen is derived from the microbial agents discussed elsewhere herein. The microbial antigen can consist of an entire inactivated microbial agent, or a fragment of a microbial agent, or even a relevant protein or polypeptide of a microbial agent expressed in a recombinant form. The microbial antigen is used to elicit immunological memory in a mammalian host immunized with such an antigen, such that upon challenge with an active microbial agent from which the microbial antigen is derived, the mammalian host can mount an effective immune response. In this way, the establishment of a microbial infection is prevented, either through a humoral immune response, a cellular immune response, or both.

A further preferred antigenic extract is comprised of a tumor-associated antigen, as discussed elsewhere herein.

A vaccine composition contemplated in the present invention therefore preferably consists of a microbial or tumor-associated antigen as discussed above, together with a therapeutically effective amount of IL-7, acting as an adjuvant to boost the establishment of immunological memory upon administration of the antigen.

The vaccine composition is preferably dissolved or dispersed in a pharmaceutically acceptable carrier, as discussed elsewhere herein.

The antigenic extract is preferably comprised of a viral antigen. That is, the antigenic extract is comprised of, for example, a heat-inactivated virus or a recombinant form of a relevant viral protein or polypeptide. For example, a live attenuated simian immunodeficiency virus (SIV, a close relative of HIV) has been used to protect rhesus monkeys against challenge with live, pathogenic SIV, thus demonstrating the usefulness of such an approach to prophylactic therapy for AIDS. See Daniel, et al., Science 258:1938–41 (1993). The use of such a live attenuated HIV virus is specifically contemplated in the present invention.

In a preferred embodiment, the viral antigen is an HIV antigen or an HSV antigen. A preferred HIV antigen is recombinant HIV envelope protein env 2-3. Steimer et al., *Vaccines* 88 347–355 (1988). A preferred HSV antigen is HSV glycoprotein D. Such viral antigens, which may be used in recombinant form, are thought to represent portions of the human immunodeficiency virus (HIV) or herpes simplex virus (HSV) important in mounting an effective immune response upon challenge with the active, intact viral agent, thus preventing infection with either HIV or HSV.

The following examples further illustrate the invention and are not to be construed as limiting of the specification and claims in any way.

EXAMPLES

Example 1

Effect of IL-7 on HIV immune response

A. Materials

Highly purified rhuIL-7 was produced in *Escherichia coli* and purified by Immunex Corporation (Seattle, Wash.). The purified rhuIL-7 (lot #2116-54) contained $3.4 \times 10^7$ U/mg and endotoxin contamination was less than 1 unit/mg protein. Peroxidase-conjugated goat antibody directed against mouse IgG was purchased from Sigma (St. Louis, Mo.). All other reagents were of analytical grades.

B. Alum-associated antigens HIV envelope protein or egg ovalbumin

Recombinant HIV envelope protein (env) or control protein, egg ovalbumin (OVA), at a concentration of 1.3 mg/ml in PBS (pH 7.4) was mixed with 9% (w/v) aluminum potassium sulfate. The alum associated antigens were precipitated by adjusting the pH of the solution to 4.0. The precipitated antigen (antigenic extract) was collected by centrifugation at 400×g for 30 min. The resulting alum-associated antigen was resuspended in PBS at 50 µg/ml and was kept frozen. Three intramuscular doses of 10 µg HIV env or OVA were given in 200 µl volume once every two weeks.

C. HIV envelope protein formulated in MTP-PE liposomes

A freeze dried preparation of lipids containing 0.23 mg MTP-PE, 7.9 mg palmitoyloleoyl phosphatidylcholine, 3.4 mg dioleoyl phosphatidylserine was suspended in 6 ml deionized $H_2O$, plus 104 µl PBS and sonicated in a bath until a translucent unilamellar liposome dispersion or suspension resulted. The suspension was filtered through a 0.2 µm-pore size membrane to sterilize the liposome and 346 µl of HIV-env (1.3 mg/ml) was added and aliquoted into 3 injection vials. The liposome suspension was frozen with continuous circular motion in an ethanol-dry ice bath. The frozen samples were lyophilized and kept at 4° C. Immediately before use, 150 µl of injection grade water was added and allowed to stand at room temperature for 15 minutes. The mixture was vortexed and 1.35 ml of injection-grade normal saline was added to obtain liposome suspension containing 50 µg/ml of HIV-env protein, 25 µg/ml MTP-PE, and 1.25 mg/ml total lipids. Each 200 µl dose contains 10 µg HIV-env, which is equivalent to that of alum-associated antigen. This protocol provided HIV env dispersed in a liposome carrier.

D. IL-7 liposome preparation

The detailed procedure of IL-7 liposome preparation has been described above. Briefly, 32 mg of egg phosphatidylcholine and 8 mg of cholesterol were mixed in 3 ml of $CHCl_3$:methanol solvent in a sterile glass tube. The organic solvent was removed under a gentle stream of $N_2$ and vacuum desiccated. To the lipid film coated on the glass tube, 7.2 ml of deionized $H_2O$ and 528 µl of PBS was added and emulsified in a bath type sonicator until a translucent unilamellar liposome suspension was obtained. The unilamellar liposome suspension was sterilized by filtration through a 0.2 µm-pore size filter. Finally, 271.7 µl of IL-7 (1.83 mg/ml) was added, and aliquoted 2 ml each into 4 injection vials. IL-7 liposomes in the vials were freeze dried with a lyophilizer and kept in a lyophilized form at 4° C. until use. Immediately before use, 0.2 ml of injection-grade water was added to hydrate the liposome at room temperature for 15 minutes with slight agitation. Then 4.8 ml of injection-grade normal saline was added to obtain the multilamellar liposome suspension containing 2 mg/ml of lipid and 25 µg/ml ($8.5 \times 10^5$ U/ml) of IL-7. Each 200 µl IP injection is equivalent to a 5 µg/dose. About 40% of the rhuIL-7 in the suspension was liposome associated and this value remained the same even after 4 days of storage at 4° C. This protocol provided IL-7 dispersed in a liposome carrier.

E. Animals and treatments

Pathogen free C3H mice were randomized into indicated treatment groups of 5–6 animals and vaccinated on days 0, 14 and 28 with 10 µg of either the alum-associated antigens or liposome-formulated antigens. Liposome-formulated IL-7 as an immune enhancer (5 µg/mouse) or empty liposomes were given on days 7, 14, 21 and 28. Fifty µl of blood samples were collected by sinus orbital bleeding on days 0, 21, 35 and 42 to determine antibody response. In addition, spleen cells were harvested on days 21, 35 and 42 from a fraction of the animals in each treatment group. These dissociated spleen cells were further analyzed for cytolytic responses against cells that express HIV env protein. Cytolytic activity of spleen cells was determined using a standard 18 hour $^3$H-protein release assay.

F. Results

The results showed that liposome-formulated antigen vaccine induced higher antibody titer than alum-associated antigen vaccine, and these antibody responses can be enhanced by administration of IL-7 liposomes. Spleen cells were harvested on days 21, 35 and 42 to evaluate cytotoxic T lymphocyte (CTL) response directed against autologous cells infected with vaccinia virus expressing HIV-env protein. Mice treated with liposome-formulated antigen expressed the highest CTL activity, regardless of whether IL-7 liposome was given as an immune potentiator (adjuvant) (FIG. 4). In contrast, spleen cells from mice vaccinated with alum-associated antigen exhibited minimal CTL response, which can be enhanced by concurrent (simultaneous) IL-7 liposome treatment (FIG. 1). Collectively, IL-7 liposome treatment enhanced the antibody production of the alum-associated or liposome-formulated env-2-3 (Tables 1 and 2) while its enhancement on CTL activity was only detected with mice vaccinated with alum-associated antigen (FIG. 1).

Table 1 shows the enhancement of the antibody response by the administration of recombinant human IL-7 in liposomes to mice immunized with alum-associated recombinant HIV envelope protein env 2-3 vaccine. Pathogen-free C3H mice were randomized into the indicated treatment groups. The immunoglobulin G (IgG) antibody response to HIV envelope protein env 2-3 was analyzed by enzyme-linked immunosorbent assay (ELISA). The data are expressed as the geometric mean plus or minus the standard error.

TABLE 1

| Treatment | | IgG Titer to Env 2-3 | |
|---|---|---|---|
| Antigen[1] | Liposomes[2] | Day 21 | Day 35/42 |
| OVA | Control | 5 ± 0 | 5 ± 0 |
| OVA | rhuIL-7 | 268 ± 101 | 268 ± 101 |
| Env | Control | 5 ± 0 | 916 ± 193 |
| Env | rhuIL-7 | 723 ± 196 | 3,283 ± 856 |

[1]Three doses of 10 μg alum-associated ovalbumin (OVA) or HIV env 2-3 (Env) were given intramuscularly on day 0, 14 and 28.
[2]Four doses of liposome-formulated recombinant human IL-7 (rhuIL-7), 5 μg per mouse or equivalent empty (control) liposomes were given intraperitoneally on day 7, 14, 21 and 28.

Table 2 shows the enhancement of the antibody response by the administration of recombinant human IL-7 in liposomes to mice immunized with recombinant HIV envelope protein env 2-3 formulated in MTP-PE liposome carriers. Pathogen-free C3H mice were randomized into the indicated treatment groups. Their IgG antibody response to HIV envelope protein env 2-3 was analyzed by ELISA. The data are expressed as in Table 1.

TABLE 2

| Treatment | | IgG Titer to Env 2-3 | |
|---|---|---|---|
| Antigen[1] | Liposomes[2] | Day 21 | Day 35/42 |
| Lipo-OVA | Control | 5 ± 0 | 5 ± 0 |
| Lipo-OVA | rhuIL-7 | 268 ± 101 | 168 ± 101 |
| Lipo-Env | Control | 2,400 ± 415 | 5,967 ± 164 |
| Lipo-Env | rhuIL-7 | 5,400 ± 1,247 | 16,200 ± 0 |

[1]Three doses of 10 μg ovalbumin (Lipo-OVA) or HIV env 2-3 (Lipo-Env), both formulated in MTP-PE liposomes, were given intramuscularly on day 0, 14 and 28.
[2]Four doses of liposome-formulated recombinant human IL-7 (rhuIL-7), 5 μg per mouse or equivalent empty (control) liposomes were given intraperitoneally on day 7, 14, 21 and 28.

Figure 3A:
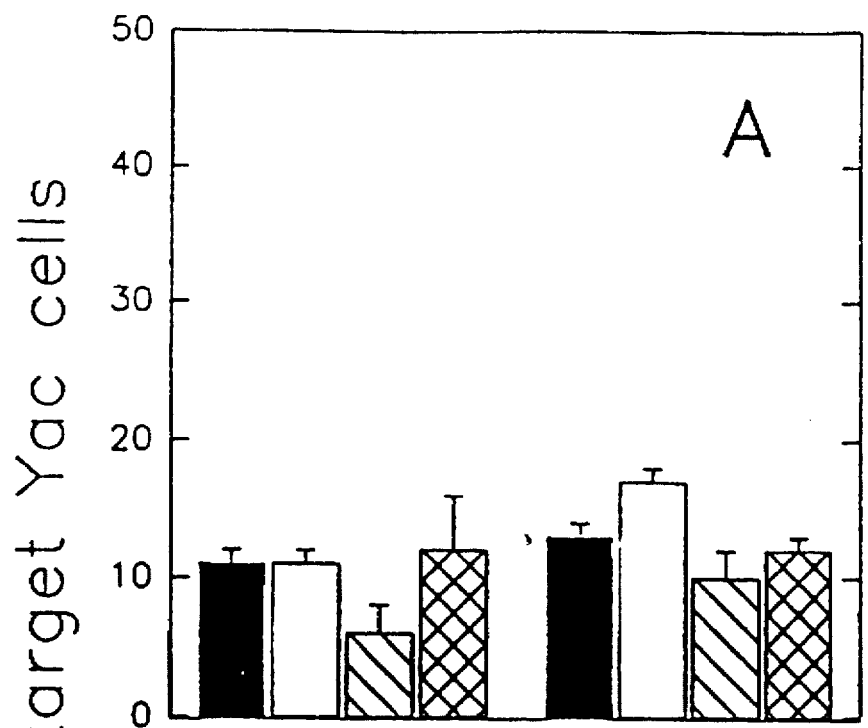
FIGS. 3A and 3B. Natural Killer cell activity of mice immunized with alum associated antigen is shown. Spleen cells from mice that had been immunized with alum associated env-2-3 (striped or hatched bars) or control (OVA) (filled or open bars), as well as given either rhuIL-7 liposomes (open or hatched bars) or empty liposomes (filled or striped bars), were used as effector cells. Cytolytic activity against NK target Yac cells were determined at effector to target cell ratios of 5:1 and 50:1 on day 21 (A) and on day 35/42 (B). The data were expressed as mean ±S.D. of each treatment group.
Figure 3B:
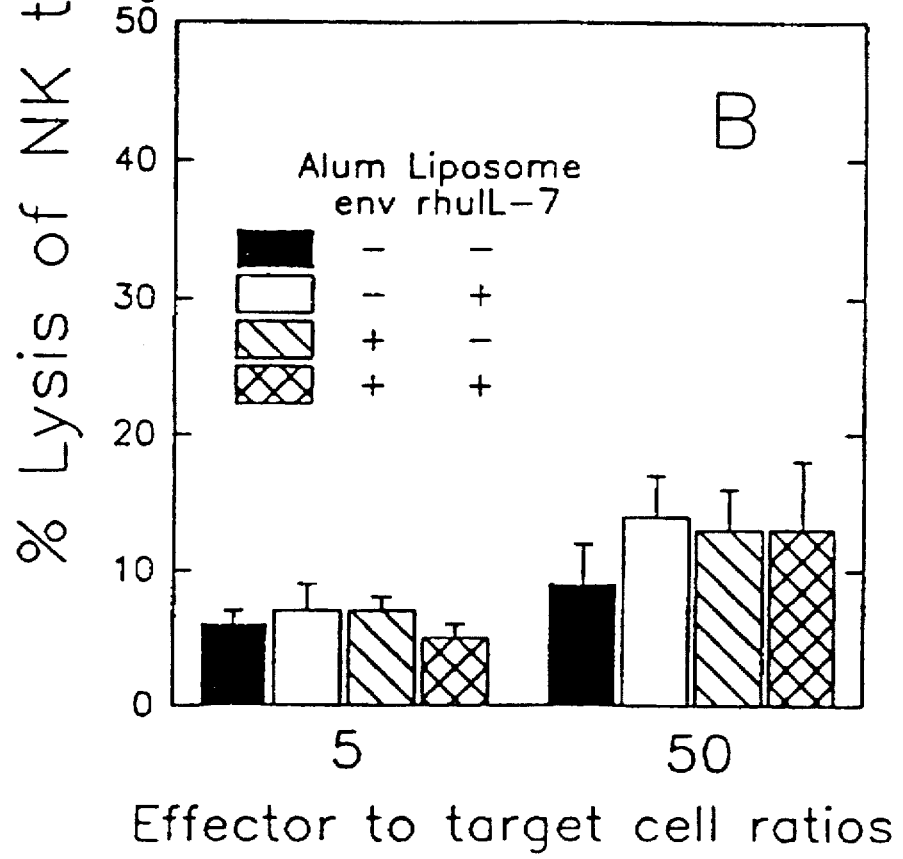

FIG. 1 shows that spleen cells from mice vaccinated with alum-associated antigen exhibited a minimal CTL response, which was enhanced by treatment with IL-7 encapsulated in liposomes. This increased CTL activity in the vaccinated mice that also received IL-7 was observed using MHC matched target cells (FIG. 1), but not MHC-mismatched target cells (FIG. 2), demonstrating the specificity of the response. This specificity was also shown by the lack of effect of IL-7 treatment on NK activity (FIG. 3).

Figures 5A, 5B, 5C, 5D:
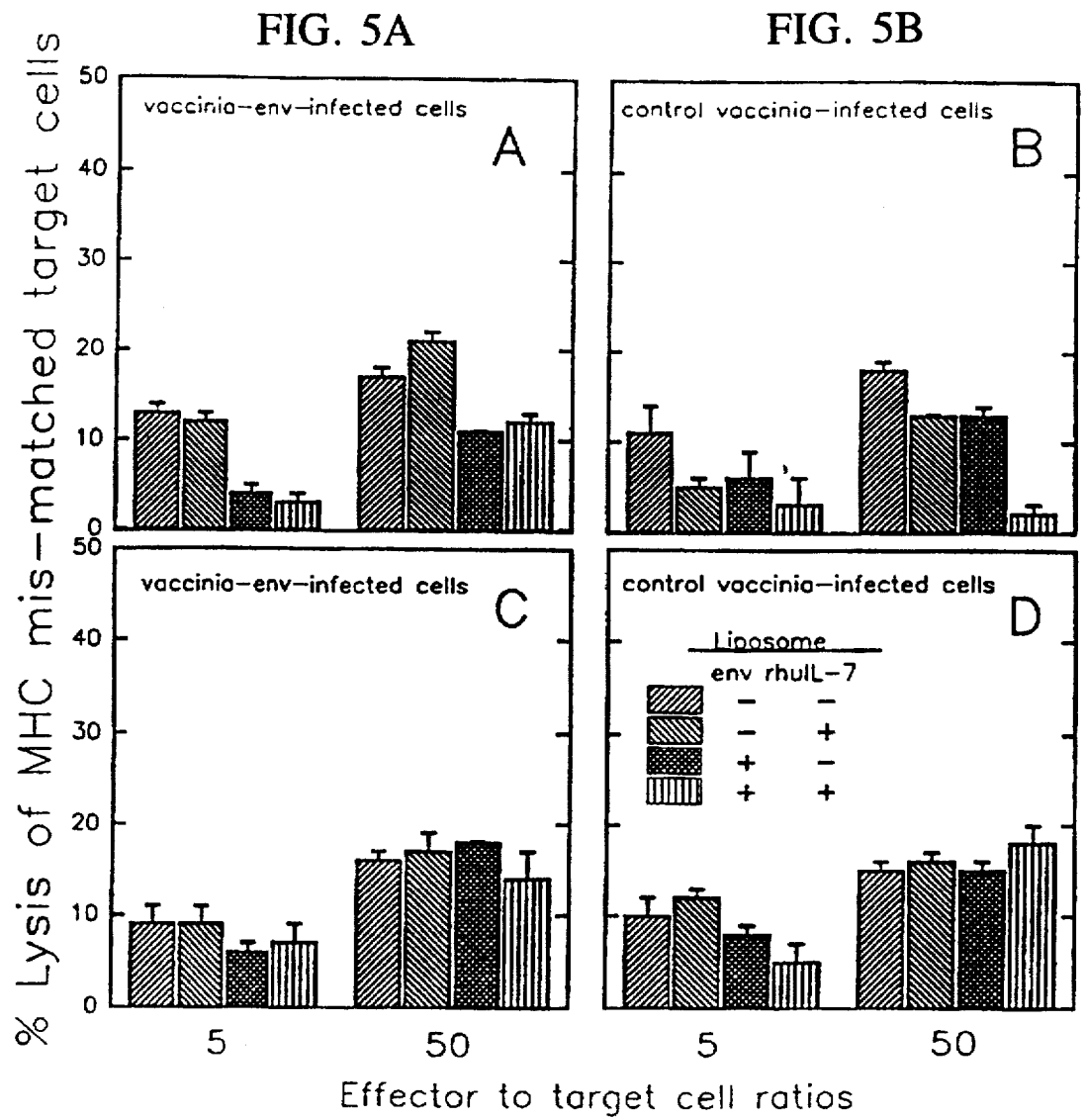
FIGS. 5A–5D. The effects of liposome encapsulated rhuIL-7 administration on cytolytic activity against vaccinia-env virus infected MHC mismatched target cells are shown. Mice were immunized with env-2-3 (hatched or lined bars) or ovalbumin formulated in MTP-PE liposomes (left or right striped bars) and were also given either rhuIL-7 liposomes (right striped or lined bars) or empty liposomes (left striped or hatched bars) as described in the treatment protocol; their spleen mononuclear cells were used as effector cells. MHC mismatched L929 cells were infected with vaccinia virus expressing env proteins (A and C) or control vaccinia virus (B and D) and were used as target cells. Cytolytic activity is expressed as percent of total lysis for spleen cells harvested on day 21 (A and B) and on day 35/42 (C and D). Data expressed were mean ±S.D. percent lysis activity of each treatment group determined at effector to target ratios of 5:1 and 50:1.
Figures 6A, 6B:
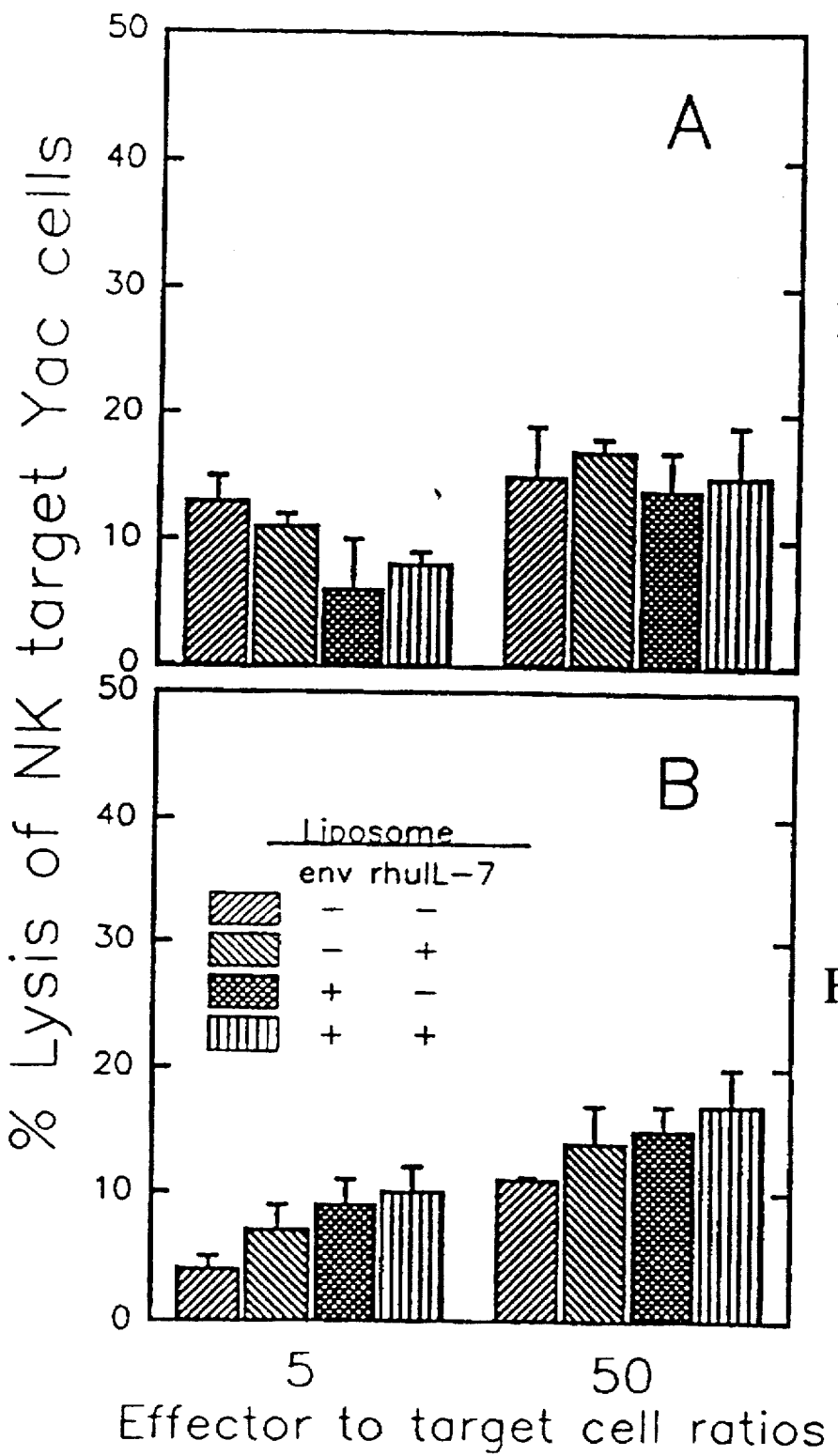
FIGS. 6A and 6B. Natural Killer cell activity of mice immunized with liposome formulated antigens is shown. Spleen cells from mice immunized with env-2-3 (hatched or lined bars) or control (OVA) (left or right striped bars), both formulated in MTP-PE liposomes, were given either rhuIL-7 liposomes (right striped or lined bars) or empty liposomes (left striped or hatched bars) and were used as effector cells. Cytolytic activity against NK target Yac cells was determined at effector to target cell ratios of 5:1 and 50:1 on day 21 (A) and day 35/42 (B). The data were expressed as mean ±S.D. of each treatment group.

In contrast with the enhancing effect of IL-7 on the CTL activity in mice that had been vaccinated with alum-associated antigen (FIG. 1), IL-7 did not enhance the CTL activity in mice that had been vaccinated with antigen in MTP-PE liposomes (FIG. 4). Specificity control experiments for the mice vaccinated with antigen in MTP-PE liposomes are shown in FIGS. 5 and 6.

Example 2

Effect of IL-7 on HSV

A. Materials

Highly purified recombinant human IL-7 (rhuIL-7) was produced in Escherichia coli and purified by Immunex (Seattle, Wash.). The purified rhuIL-7 (lot #2664-6-1) contained $4\times10^7$ U/mg; endotoxin contamination was less than 1 unit/mg protein. Peroxidase-conjugated goat antibodies directed against guinea pig IgG and IgA were purchased from Sigma (St. Louis, Mo.); RPMI 1640 and antibiotics were purchased from Gibco BRL (Grand Island, N.Y.); and fetal calf serum (FCS) was purchased from Hyclone (Logan, Utah). Other reagents were of analytical grades.

B. Alum-associated HSV glycoprotein antigen gD

Highly purified recombinant HSV glycoprotein D (gD), produced in CHO cells (kindly provided by Dr. R. L. Burke of Chiron Corporation), was used in these studies. HSV-gD at a concentration of 1.3 mg/ml was mixed with equal volumes of 9% (w/v) aluminum potassium sulfate. The antigen was precipitated by adjusting the pH to 4.0, and the precipitated antigen was collected by centrifugation. Then, alum-associated HSV-gD was resuspended at 60 μg/ml in PBS. Three doses of 12 μg antigen were given in a 200 μl volume once every two weeks. This protocol provided HSV gD antigen vaccine.

C. RhuIL-7 liposome preparation 28.8 mg of lipids composed of egg phosphatidyl choline:cholesterol (8:2 w/w) dissolved in $CHCl_3$ or $CHCl_3:CH_3OH$ (1:1, v/v) were mixed and dried under a gentle stream of $N_2$ gas at room temperature, vacuum desiccated for 30 min, and resuspended in 4 ml of injection-grade $H_2O$ plus 40 μl of sterile PBS. After vortexing, the mixture was emulsified in a bath-type cylindrical sonicator (Laboratory Supplies, Inc., Hickville, N.Y.) for 15 min at room temperature to prepare a translucent single layer of lipid membrane liposome suspension. This suspension was sterilized by passage through a 0.2 μm pore-size filter, followed by the addition of $1.4\times10^8$ U of rhuIL-7 in 1.96 ml of 50 mM sodium acetate, pH 4.7, 0.4M sodium chloride. The mixture was divided into 4×1.5 ml aliquots, frozen in an ethanol-dry ice bath, lyophilized, and stored at 4° C. Lyophilized liposomes were rehydrated immediately prior to use by the addition of 0.5 ml of injection-grade $H_2O$. The mixture was vortexed and allowed to stand at room temperature for 15 min to generate multilamellar vesicles. Finally, 3 ml of injection-grade normal saline was added to obtain a liposome suspension containing 2.4 mg/ml of lipids and $9.8\times10^6$ U/ml of rhuIL-7. The efficiency of liposome encapsulation was measured immediately following rehydration; 40±4% of the rhuIL-7 was encapsulated; the remainder was present in the dispersion in a soluble form and not liposome-associated. Even after 100 hours storage at 4° C., 37±3% of the IL-7 remained entrapped in the liposomes. Approximately 200 μl of the rhuIL-7 liposome suspension was given to each animal, corresponding to 5.6×10⁶ U/kg dose.

D. Animals and rhuIL-7 administration

Female guinea pigs, Hartley strain (250–300 g), approximately 3 months old, were purchased from Tyler Caviary (Bellevue, Wash.). These guinea pigs were given twice-daily subcutaneous (s.c.) injections of either rhuIL-7 or saline (placebo) in an approximately 200 µl volume according to their weight. For each injection, soluble rhuIL-7 was diluted from the stock (3×10⁷ U/ml) immediately before use. Where indicated, rhuIL-7 liposomes were also given via a subcutaneous route in approximately 200 µl. Soluble rhuIL-7 was given on a twice-daily schedule, while liposome-formulated rhuIL-7 was given on a weekly schedule.

E. Proliferation of guinea pig and human peripheral blood monocytes

Peripheral blood mononuclear cells (PBMCs) of untreated guinea pigs or of healthy human subjects were isolated from the blood samples using either human or guinea pig Ficoll-Hypaque (Pharmacia, Piscataway, N.J.) gradient (specific gravity=1.09) and centrifuged at 400×g for 30 min. PBMCs that had banded at the interface were collected and washed twice with RPMI 1640 medium. When needed, the PBMCs were separated into plastic-adherent and non-adherent cells by first incubating 5×10⁶ cells in 10 ml of RPMI supplemented with 1.72% $HCO_3$ (w/v), 25 mM HEPES, 0.05 mM β-mercaptoethanol, and 10% FCS (v/v) (referred to as growth medium). After 2 hours of attachment time, the non-adherent cells were removed and the adherent cells were washed three times with growth medium. PBMCS, non-adherent cells, or adherent cells were loaded at 2×10⁵ cells/100 µL growth medium in 96-well plates (Flow Lab, McLean, Va.) and were incubated with 100 µL rhuIL-7 containing growth medium for 6 days in a 37° C., 5% $CO_2$ incubator. For antibody blocking experiments, rhuIL-7 was pre-incubated with equal volumes of rabbit antiserum (containing 1.07×10⁵ U of rhuIL-7 neutralizing activity per ml) for 1 hour before being added to the cells. On the 6th day, these cells were pulsed with 1 µCi/well of ³H-TdR for 6 hours to assess the degree of cell proliferation. ³H-TdR that had incorporated into cellular DNA was collected on glass fibers with a cell harvester (Cambridge Tech., Watertown, Mass.), and the degree of proliferation was determined by scintillation counting of radioactivity. Data collected were expressed as mean ±SD of the quadruplicates.

F. Circulating blood cell counts

At indicated time intervals, guinea pigs were intracardially bled (under anesthesia) and the blood samples were sent to a central lab (Phoenix Lab, Seattle, Wash.). The differential counts were determined by a blinded investigator with no knowledge of the treatment groups. Data are expressed as the mean ±SD of each treatment group.

G. HSV-2 infection and scoring

On day 7 of the twice-daily injections of rhuIL-7 (experiment 1), or 14 days after the 3rd dose of HSV-gD vaccination (experiment 2), all animals were intravaginally infected with HSV-2 (MS strain). For experiment 1, rhuIL-7 was given twice daily for 3 additional days, post HSV-2 infection, totalling 10 days and 20 doses. Techniques of HSV-2 inoculation, as well as scoring of the HSV-2 lesions, are well known in the art. Briefly, guinea pigs were inoculated with 5×10⁴ plaque forming units (pfu) of HSV-2 (MS strain), delivered in 0.1 ml of RPMI medium through a plastic catheter attached to a syringe, followed by insertion of a gel foam to retain the fluid. These animals were monitored and scored blind daily. The severity of clinical disease was scored ("lesion score") as follows: 0, no disease; 1, erythema, vesicles, or ulcers restricted to the introitus; 2, a few vesicles on the perineum; 3, confluent lesions covering most of the perineum and/or urinary retention; and 4, extensive necrotic lesions and/or hind leg paralysis or encephalitis. Animals were bled on the day before and 14 days after HSV-2 infection for immunological analysis. To evaluate the virus shedding and IgA antibody level, vaginal swabs were taken on the day before and every two days after HSV-2 infection. Vaginal swab samples were collected in sterile tubes using pre-wetted cotton swabs placed in 1 ml of RPMI containing 500 U/ml penicillin and 500 µg/ml fungizone. These animals were monitored for acute disease development over the next 20 days, and data collected were presented as days post-HSV-2 challenge.

H. Anti-HSV-gD antibody titer

HSV-gD-specific antibody titers were determined by enzyme-linked immunosorbent assay (ELISA). Microtiter plates were coated with cell lysate infected with vaccinia virus expressing HSV-gD. The antigen control wells contained cell lysate infected with control vaccinia virus. The excess antigen was removed and nonspecific binding sites were blocked with 1% bovine serum albumin (w/v) prior to the addition of plasma or vaginal swab samples. These samples were inactivated by incubation at 56° C. for 5 min before assaying them for antibody titer. Plasma or vaginal swab samples were serially diluted 5 fold to determine the antibody titer. For plasma samples, enzyme-linked antibody against guinea pig IgG was used to determine the IgG titer, whereas, for vaginal swab, enzyme-linked antibody against guinea pig IgA was used to detect the secretory IgA antibody. Data are expressed as the geometric mean ±SE.

I. Statistical analysis

Survival and HSV-2 lesion scores were analyzed with student t-test. The overall course of HSV-2 infection (FIG. 9) was analyzed with paired t-test.

J. Results

1. Stimulation of guinea pig PBMCs by rhuIL-7

Figure 7:
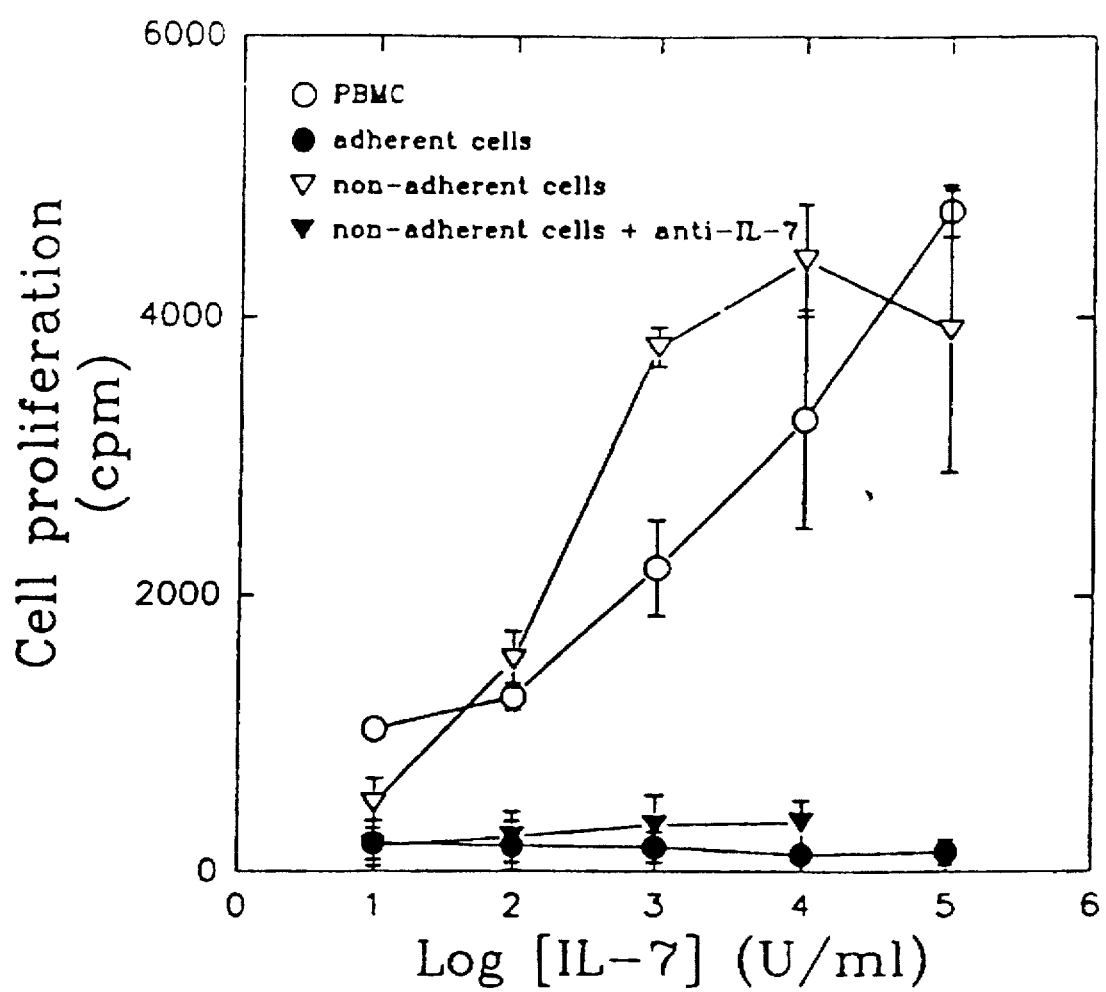
FIG. 7. The stimulation of guinea pig peripheral blood mononuclear cells (PBMCs) by rhuIL-7 is shown. PBMCs (open circles), adherent cells (filled circles), or non-adherent cells (open triangles) from the peripheral blood of a guinea pig were stimulated with the indicated concentration of rhuIL-7 for six (6) days, and the degree of cell proliferation was expressed as counts per minute (cpm) of $^3$H-TdR incorporation into cellular DNA. The non-adherent cells of guinea pig PBMCs were also incubated with rhuIL-7 that had been neutralized with rabbit antiserum against rhuIL-7 (filled triangles). Each sample was done in quadruplicate, and the error bar represents a S.D. from the mean.

PBMCs of human subjects or guinea pigs were stimulated with various concentrations of rhuIL-7 for 6 days, and cell proliferation was assessed. The results of a representative experiment are shown in Table 3. RhuIL-7 stimulated guinea pig PBMCs in a concentration-dependent manner. Approximately 100 U/ml rhuIL-7 is minimally required to detect cell proliferation. PBMCs from 6 animals were tested, and the trends of the rhuIL-7 titration curves were reproducible, although the magnitude of the ³H-TdR incorporation did vary. When the adherent cells in PBMCs were separated, it was found that a considerable portion of the proliferation activity detected with PBMCs was found in the non-adherent cell fraction (FIG. 7 and Table 3), indicating that the rhuIL-7-responsive cells were probably T and B cells. The molecular specificity of rhuIL-7 on the non-adherent cells was further demonstrated by the ability of the anti-rhuIL-7 serum to inhibit the rhuIL-7-dependent cell proliferation (FIG. 7). Parallel control experiments were done with human PBMCs (FIG. 7), and the plastic non-adherent population gave an rhuIL-7 proliferative response similar to that of guinea pig cells. Therefore, it was concluded that rhuIL-7 cross-stimulates guinea pig PBMCs (specifically, plastic non-adherent T and B lymphocytes) to proliferate in vitro.

TABLE 3[a]

| | rhuIL-7 (Units/ml$^{-1}$) | | | | |
|---|---|---|---|---|---|
| | $10^4$ | $10^3$ | 102 | 10 | 0 |
| | Guinea Pig | | | | |
| Total PBMC | 3028 ± 476 | 2075 ± 458 | 2142 ± 929 | 1024 ± 454 | 485 ± 5 |
| Non Adhr | 1875 ± 461 | 1242 ± 120 | 1356 ± 604 | 813 ± 173 | 636 ± 202 |
| | Human | | | | |
| Total PBMC | 6706 ± 989 | 5994 ± 461 | 4787 ± 595 | 4092 ± 764 | 1739 ± 339 |
| Non Adhr | 5114 ± 278 | 4922 ± 480 | 4751 ± 707 | 2399 ± 786 | 1560 ± 367 |

[a]Guinea pig or human peripheral blood mononuclear cells (PBMC) were isolated from blood by the Ficoll-Hypaque gradient centrifugation method. PBMCs were further separated as plastic-adherent and non-adherent (Non Adhr) cells. $2 \times 10^5$ cells of indicated subsets were incubated with rhuIL-7 for 6 days and cell proliferation was measured by the $^3$H-TdR incorporation assay. The expressed data represent the mean ± SD of quadruplicate examples.

2. Induction of guinea pig white blood cells by rhuIL-7

To determine the immunopharmacologic activity of rhuIL-7, soluble rhuIL-7 or a sustained-release formulation of rhuIL-7 (dispersed in liposomes) were administered to the guinea pigs. Preliminary experiments indicated that subcutaneously introduced soluble drug was cleared within a few hours. Hence, rhuIL-7 was given in a twice-daily schedule for 7 days, and white blood cell count was determined on day 7, 2 hours after the first dose of rhuIL-7 for that day. As shown in Table 4, experiment 1, administration of rhuIL-7 increased the white blood cell concentration of the treated guinea pigs in a dose-dependent manner. At $2.4 \times 10^6$ U/kg dose, a significant increase was detected in the white blood cell concentration compared with that of placebo-treated animals (3.94±0.71 vs. 7.34±1.33×10$^3$ cells/mm$^3$; p=0.002). Further analysis showed that a significant increase in the blood lymphocyte concentration (2,584±408 vs. 6,170±1,191 cells/mm$^3$; p=0.0005) was the major contributor to the observed increase in white blood cell number (Table 4, experiment 1). Animals treated with a 3-fold lower dose, $8 \times 10^5$ U/kg, of rhuIL-7 also exhibit an increase in the blood-lymphocyte concentration (2,584±408 vs. 3,560±726 cells/mm$^3$; p=0.047). However, in vivo administration of rhuIL-7 did not increase monocyte, eosinophil, or neutrophil numbers in guinea pigs.

Next, rhuIL-7 liposomes were used as a sustained-release vehicle to reduce the frequency of repeated rhuIL-7 administration. Preliminary experiments indicated that rhuIL-7 liposomes administered subcutaneously at $5.6 \times 10^6$ U/kg remained detectable for more than 48 hours (compared with a couple of hours for soluble rhuIL-7). As shown in Table 4, experiment 2, one week after the 2-weekly injections, rhuIL-7 liposome treatment increased the guinea pig white blood cells, specifically the lymphocyte concentration in the blood (about 46% increase; p<0.05). The magnitude of elevated lymphocyte concentration observed in the treated animals was comparable to the twice-daily injections of $8 \times 10^5$ U/kg×7 days (Table 4, experiment 1). Taken together, these data shown that in vivo administration of rhuIL-7 increases guinea pig white cell concentration, specifically the lymphocyte population.

TABLE 4

| Treatment | RhuIL-7 (U/kg) | Total White[c] Blood Cells (×10$^3$/mm$^3$) | Total Lymphocyte (per mm$^3$) |
|---|---|---|---|
| Experiment 1: Twice-daily SC administrations of rhuIL-7[a] | | | |
| Placebo | 0 | 3.94 ± 0.71 | 2,584 ± 408 |
| RhuIL-7 | $8 \times 10^5$ | 5.08 ± 1.19 | 3,560 ± 726 |
| RhuIL-7 | $2.4 \times 10^6$ | 7.34 ± 1.33 | 6,170 ± 1,191 |
| Experiment 2: Two weekly SC administrations of rhuIL-7 liposomes[b] | | | |
| Placebo | 0 | 4.17 ± 0.74 | 2,247 ± 290 |
| RhuIL-7 Liposomes | $5.6 \times 10^6$ | 5.77 ± 1.44 | 3,274 ± 337 |
| HSV-gD | 0 | 3.70 ± 0.37 | 2,295 ± 270 |
| HSV-gD + rhuIL-7 Liposomes | $5.6 \times 10^6$ | 4.90 ± 0.16 | 2,774 ± 175 |

[a]RhuIL-7 was given subcutaneously (SC) twice daily at the indicated dose for 7 days and a differential blood cell count was determined.
[b]A differential blood cell count was determined one week after the second dose of rhuIL-7 liposomes. Placebo and HSV-gD group received empty liposomes (i.e., without rhuIL-7).
[c]Total cell counts were expressed as mean ± SD of the treatment group.

3. protective effects of rhuIL-7 against HSV-2

To determine the in vivo antiviral activity of rhuIL-7, guinea pig models of genital HSV-2 infection were used. Animals treated with rhuIL-7 alone, or in combination with alum-associated HSV-gD, were challenged with $5 \times 10^4$ pfu of HSV-2, a sublethal dose for these guinea pigs. The guinea pigs were monitored daily during the primary course of HSV-2 infection for 14 days, and the results are summarized in Table 5. In the first experiment, guinea pigs were given twice-daily subcutaneous injections of 0, $8.0 \times 10^5$, or $2.4 \times 10^6$ U/kg of rhuIL-7 for 7 days before HSV-2 infection. The guinea pigs were given 3 additional days of rhuIL-7 treatment after HSV-2 infection, and the results are summarized in Table 5, experiment 1. By day 14 after HSV-2 infection, no difference in the mean HSV-2 lesion score was observed. However, a trend toward increased mortality rate was noted for both low ($8.0 \times 10^5$ U/kg) and high ($2.4 \times 10^6$ U/kg) dose rhuIL-7 treated groups (50% and 30% survival, respectively, compared to 70% for placebo; Table 5, experiment 1).

The antigen-specific immune improvement activity of rhuIL-7 was tested by giving 4 weekly doses of rhuIL-7 liposome ($5.6 \times 10^6$ U/kg given on days 7, 14, 21 and 28), overlapping the three doses of alum-associated HSV-gD (12 µg/dose given on days 0, 14 and 28; Table 5, experiment 2). These animals were infected with the same amount of HSV-2 ($5 \times 10^4$ pfu) on day 14 after the last dose of HSV-gD (day 42 of the experiment). Again a lower survival rate for animals in the rhuIL-7 liposome-treated group was observed (38% vs. 63% for placebo group; experiment 2), while the rate for placebo-treated animals was comparable to experiment 1. All the animals treated with HSV-gD survived regardless of whether they were given rhuIL-7 liposomes or empty liposomes.

Figure 8:
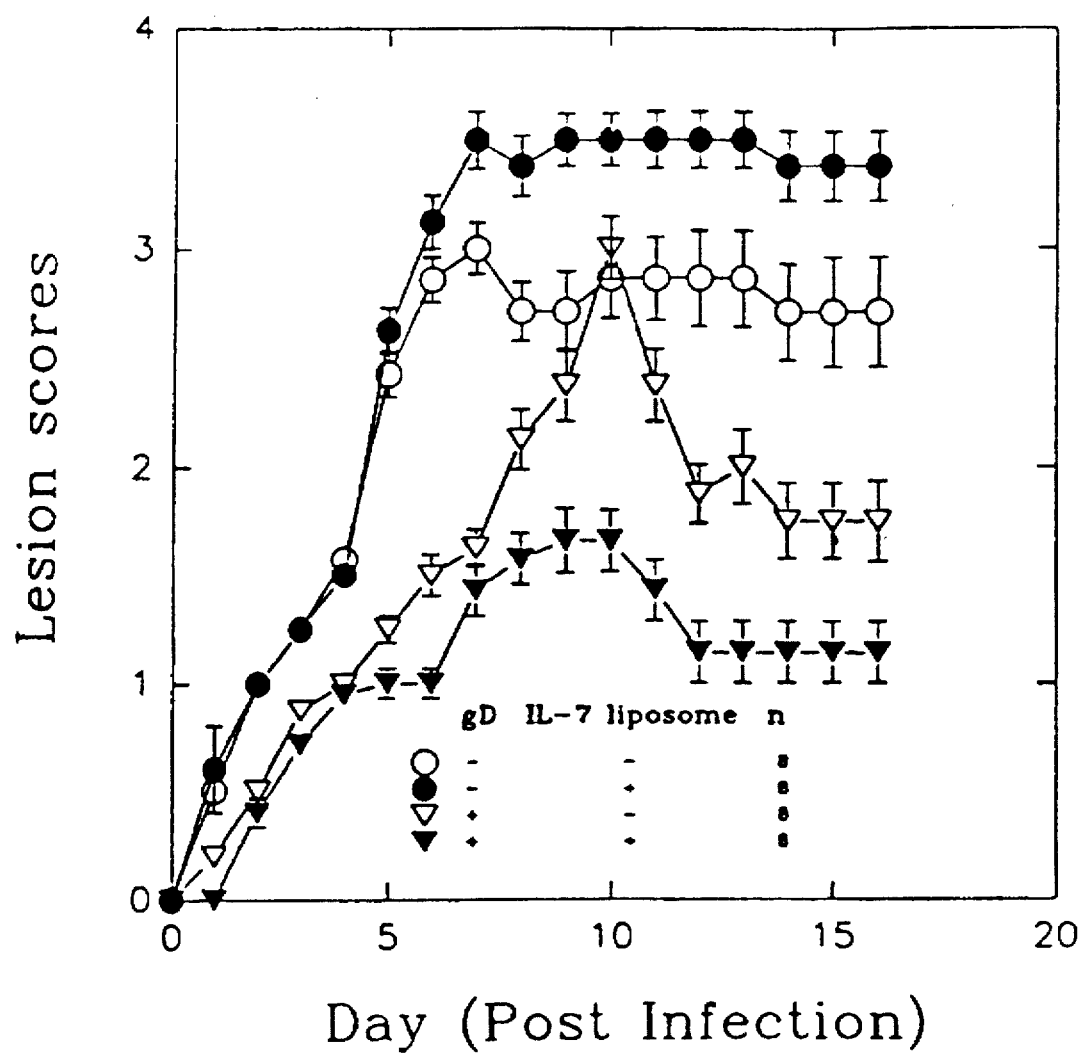
FIG. 8. The reduction of HSV-2 lesion severity by HSV-gD and rhuIL-7 liposome treatments is shown. Guinea pigs treated with alum-precipitated HSV-gD (open or filled triangles) or placebo (open or filled circles) were also given either rhuIL-7 liposomes (filled triangles or circles) or empty liposomes (open triangles or circles) as adjuvant. All guinea pigs were inoculated with 5×10$^4$ pfu of HSV-2, and the clinical lesion scores of each group are presented as mean ±(standard error) S.E. for the acute phase of HSV infection.

Analysis of HSV-2 lesion severity indicates that the animals treated with the HSV-gD and rhuIL-7 liposome combination experienced a milder course of HSV-2 infection than animals treated with HSV-gD and empty liposomes (Table 5, experiment 2, and FIG. 8). As shown in FIG. 8, both HSV-gD and HSV-gD-plus-rhuIL-7-liposome-treated groups exhibit a delay in the development of HSV-2 lesions. For this sublethal HSV-2 challenge, only animals treated with a combination of rhuIL-7 liposome and HSV-gD exhibited a significant reduction in HSV-2 lesion score at day 14 post-infection (p<0.05 vs. placebo group; Table 5, experiment 2). This shows the improvement of the potency of the HSV gD vaccine by the administration of IL-7.

Figure 9:
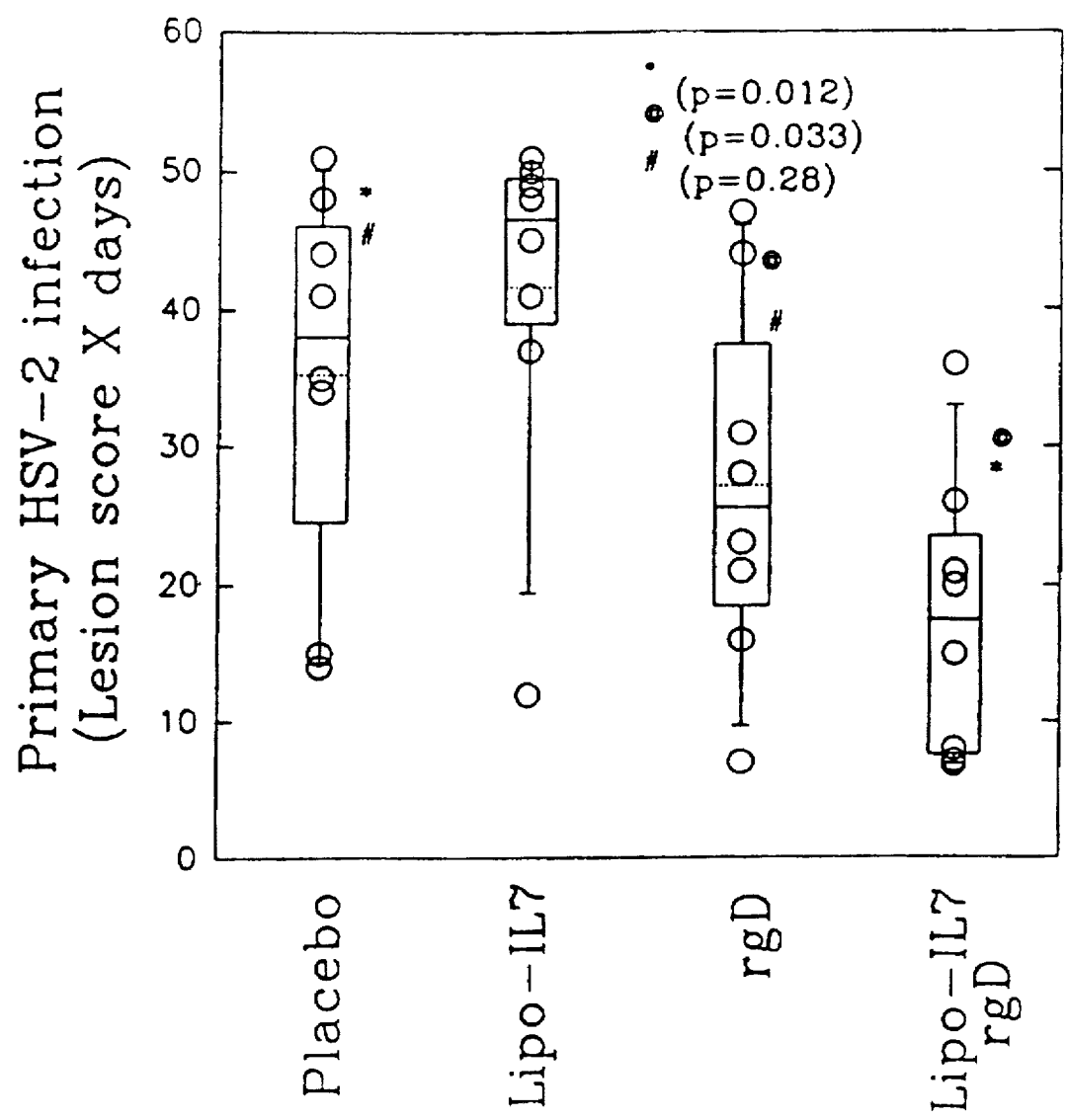
FIG. 9. The effects of HSV-gD and rhuIL-7 treatments on primary HSV-2 infection are shown. The overall course of acute HSV-2 infection for each animal is presented as the sum of the lesion scores for each day that the animal exhibited lesions. The scatter plot data for each group is also presented as a box-plot. Paired t-test was used to compare the results of different treatments. P values for placebo vs. HSV-gD (#), placebo vs. HSV-gD plus rhuIL-7 liposomes (*), and HSV-gD vs. HSV-gD plus rhuIL-7 liposomes (@) were 0.28, 0.012 and 0.033, respectively.

The primary course of HSV-2 infection was further evaluated based on the sum of the lesion score for each day that the animal exhibited lesions. As shown in FIG. 9, only animals vaccinated with HSV-gD and rhuIL-7 liposomes exhibited a significantly less severe course of HSV-2 infection compared with the placebo group (p=0.012). Although the HSV-gD-treated group experienced a significantly milder course of HSV-2 infection compared with the rhuIL-7 liposome-treated group (p<0.05), the differences were not significant when compared with the placebo group (p=0.28). Taken together, these data indicated that when given in combination with HSV-gD, rhuIL-7 liposomes elicit enhanced HSV-gD vaccine potency, resulting in a significantly reduced severity of primary HSV-2 infection.

TABLE 5

| | Day 14 post HSV-2 infection[c] | | | |
|---|---|---|---|---|
| Treatment | RhuIL-7[a] (U/kg) | n[b] | % Survival | Lesion Score Mean ± SE |
| Experiment 1: Twice daily S.C. administrations of rhuIL-7[d] | | | | |
| Placebo | 0 | 10 | 70 | 2.7 ± 0.3 |
| RhuIL-7 | 8 × 10$^5$ | 10 | 50 | 3.2 ± 0.4 |
| RhuIL-7 | 2.4 × 10$^5$ | 10 | 30 | 2.7 ± 0.9 |
| Experiment 2: Four weekly administrations of rhuIL-7 liposomes[e] | | | | |
| Placebo | 0 | 8 | 63 | 2.8 ± 0.3 |
| RhuIL-7 liposomes | 5.6 × 10$^6$ | 8 | 38 | 3.5 ± 0.2 |
| HSV-gD | 0 | 8 | 100 | 1.8 ± 0.2 |
| HSV-gD + rhuIL-7 liposomes | 5.6 × 10$^6$ | 8 | 100 | 1.1 ± 0.1 |

[a]RhuIL-7, either in free soluble form (experiment 1) or liposome-formulated, sustained-release form (experiment 2), given subcutaneously (S.C.) at the indicated dose.
[b]Total number of animals in each treatment group.
[c]The survival of guinea pigs at day 14 post HSV-2 infection (5 × 10$^4$ pfu/animal was expressed as percent survival.
[d]Experiment 1: RhuIL-7 was given twice daily for 10 days, and HSV-2 infection was done on day 7 of rhuIL-7 administration.
[e]Experiment 2: RhuIL-7 liposome, was given weekly for 4 weeks, overlapping biweekly injections of alum-precipitated HSV-gD. For details, refer to Sections A through H above.

4. Immunological responses of rhuIL-7 liposome-treated animals

Guinea pigs vaccinated with HSV-gD and/or rhuIL-7 liposomes were bled before HSV infection to determine the enhancement of immune response by the treatments. Blood cells from three representative animals of each group were tested for their lymphocyte proliferative response to the immunized antigen HSV-gD. Their PBMCs were also tested for cell-mediated cytotoxicity against virus-infected cells. No significant induction in lymphocyte proliferative response to HSV-gD was detected for animals treated with either HSV-gD alone or in combination with rhuIL-7 liposomes. No PBMCs from either the HSV-gD or the HSV-gD-plus-rhuIL-7 liposome group exhibited enhanced cell-mediated cytotoxic activity against either HSV-2-infected cells or vaccinia-gD (vaccinia virus-expressing HSV-gD antigen)-infected guinea pig cells. These results suggest that alum-associated HSV-gD minimally induces the cell-mediated immune response and that adjunct rhuIL-7 liposome administration does not significantly improve this immune function.

To assess the antibody response prior to HSV-2 challenge, the levels of blood IgG antibody and vaginal secretory IgA directed against HSV-gD were determined. As shown in Table 6, a significantly higher IgG antibody titer against HSV-gD was detected for the animals that were treated with HSV-gD plus rhuIL-7 liposomes as compared with animals treated with HSV-gD alone (6,982±1,052 vs. 23±6; p<0.05). A similar, but less prominent, enhancement of HSV-gD IgA antibody titer was observed for the HSV-gD-plus-rhuIL-7 liposome combination group (188±38 vs. 1±0 for HSV-gD; p<0.05). Taken together, these results indicate that rhuIL-7 liposomes enhance antibody production in response to immunizing guinea pigs with alum-associated HSV-gD vaccine. This immunological enhancement parallels the increased potency against primary HSV-2 infection in guinea pigs.

TABLE 6

| | | Anti-HSV-gD titer at day 42[a] | |
|---|---|---|---|
| Treatment | n[b] | IgG[c] | IgA[d] |
| Placebo | 8 | 2 ± 0 | 3 ± 0 |
| RhuIL-7 liposomes | 8 | 2 ± 0 | 3 ± 0 |
| HSV-gD | 8 | 23 ± 6 | 1 ± 0 |
| HSV-gD + rhuIL-7 liposomes | 8 | 6982 ± 1052 | 188 ± 38 |

[a]Anti-HSV-gD titer was determined by ELISA for the presence of IgG and IgA antibody, as described in Sections A through H above, for the samples collected on day 42 (experiment 2): 14 days after the third HSV-gD injection.
[b]Total number of animals in each treatment group.
[c]IgG antibody titer was determined on the plasma samples, and was expressed as geometric mean ± S.E.
[d]IgA antibody titer was determined on the vaginal swab sample, and was expressed as geometric mean ± S.E.

The foregoing specification, including the specific embodiments and examples is intended to be illustrative of the present invention and is not to be taken as limiting. Numerous other variations and modifications can be effected without departing from the true spirit and scope of the present invention.

We claim:

1. A method of increasing humoral immunity of a vaccine in a host mammal comprising the steps of
   (a) administering to said host mammal a therapeutically effective amount of a vaccine and
   (b) administering to said host mammal an amount of IL-7 sufficient to increase humoral immunity, thereby increasing antibody production to said vaccine in the host.

2. The method of claim 1 wherein said vaccine prevents a microbial infection.

3. The method of claim 2 wherein said microbial infection is caused by a microbe selected from the group consisting of viruses, fungi, yeast, bacteria and protozoa.

4. The method of claim 2 wherein said microbial infection is caused by Herpes Simplex Virus.

5. The method of claim 1 wherein said IL-7 is recombinant IL-7.

6. The method of claim 5 wherein said recombinant IL-7 is selected from the group consisting of murine recombinant IL-7 and human recombinant IL-7.

7. The method of claim 1 wherein said IL-7 is dissolved or dispersed in a pharmaceutically acceptable carrier.

8. The method of claim 7 wherein said pharmaceutically acceptable carrier is in the form of a lipid dispersion.

9. The method of claim 8 wherein said lipid dispersion is comprised of liposomes.

10. The method of claim 1 wherein said administration of said vaccine and said administration of said IL-7 occurs simultaneously.

11. The method of claim 1 wherein said administration of said vaccine and said administration of said IL-7 occurs sequentially.

12. A method of increasing humoral immunity of a vaccine comprising adding an amount of IL-7 to a vaccine sufficient to increase humoral immunity.

13. The method of claim 12 wherein said vaccine prevents microbial infection.

14. The method of claim 13 wherein said microbial infection is caused by a microbe selected from the group consisting of viruses, fungi, yeast, bacteria and protozoa.

15. The method of claim 13 wherein said microbial infection is caused by Herpes Simplex Virus.

16. The method of claim 13 wherein said IL-7 is recombinant IL-7.

17. The method of claim 16 wherein said recombinant IL-7 is selected from the group consisting of murine recombinant IL-7 and human recombinant IL-7.

18. The method of claim 13 wherein said IL-7 is dissolved or dispersed in a pharmaceutically acceptable carrier.

19. The method of claim 18 wherein said pharmaceutically acceptable carrier is in the form of a lipid dispersion.

20. The method of claim 19 wherein said lipid dispersion is comprised of liposomes.

* * * * *